United States Patent
Kroekel et al.

(10) Patent No.: US 9,335,264 B2
(45) Date of Patent: May 10, 2016

(54) DETECTION OF RAINDROPS ON A PANE BY MEANS OF A CAMERA AND LIGHTING

(75) Inventors: Dieter Kroekel, Eriskirch (DE); Radhakrishna Chivukula, Bietigheim-Bissingen (DE)

(73) Assignee: Conti Temic microelectronic GmbH, Nuremberg (DE)

( * ) Notice: Subject to any disclaimer, the term of this patent is extended or adjusted under 35 U.S.C. 154(b) by 253 days.

(21) Appl. No.: 13/885,552

(22) PCT Filed: Sep. 20, 2011

(86) PCT No.: PCT/DE2011/001749
§ 371 (c)(1),
(2), (4) Date: May 15, 2013

(87) PCT Pub. No.: WO2012/092911
PCT Pub. Date: Jul. 12, 2012

(65) Prior Publication Data
US 2013/0235381 A1    Sep. 12, 2013

(30) Foreign Application Priority Data

Nov. 30, 2010   (DE) .......................... 10 2010 052 968

(51) Int. Cl.
*G01N 21/55* (2014.01)
*H01J 40/14* (2006.01)
(Continued)

(52) U.S. Cl.
CPC .............. *G01N 21/55* (2013.01); *B60S 1/0844* (2013.01); *G01N 21/552* (2013.01); *G06K 9/00791* (2013.01); *G01N 2021/435* (2013.01)

(58) Field of Classification Search
CPC .... B60S 1/0844; B60S 1/0822; B60S 1/0833; G01N 21/55; G01N 21/552; G01N 2021/435; B60R 1/00

USPC .............. 356/445; 348/E5.034, E5.085, 148; 340/602, 601; 250/214 R, 574, 227, 25, 250/341.8
See application file for complete search history.

(56) References Cited

U.S. PATENT DOCUMENTS 4,515,443 A    5/1985  Bly
4,741,605 A    5/1988  Alfredsson et al.
(Continued)

FOREIGN PATENT DOCUMENTS

CN    1657905 A    8/2005
CN    101896375 A    11/2010
(Continued)

OTHER PUBLICATIONS

Partial English translation of Japanese Office Action in Japanese Patent Application No. 2013-542369, mailed Jan. 7, 2015, 1 page.
(Continued)

*Primary Examiner* — Tarifur Chowdhury
*Assistant Examiner* — Sunghee Y Gray
(74) *Attorney, Agent, or Firm* — W. F. Fasse

(57) ABSTRACT

A device and a method for detecting rain on a pane, e.g. of a motor vehicle, use a camera or other light sensor and a lighting source. The camera is disposed behind an inner surface of the pane and focused onto a far range that lies in front of an outer surface of the pane. The lighting source generates a source light beam and directs it onto the inner surface of the pane such that at least one resultant reflected beam (r2; r2') that is reflected from the outer surface of the pane impinges on the camera. The light quantity of the at least one resultant reflected beam is measured by the camera.

24 Claims, 7 Drawing Sheets

(51) Int. Cl.

| | | |
|---|---|---|
| *G02B 6/42* | (2006.01) | |
| *G01J 5/02* | (2006.01) | |
| *G01N 15/06* | (2006.01) | |
| *G01W 1/00* | (2006.01) | |
| *G08B 21/00* | (2006.01) | |
| *H02P 7/00* | (2006.01) | |
| *B60S 1/08* | (2006.01) | |
| *G01N 21/552* | (2014.01) | |
| *G06K 9/00* | (2006.01) | |
| *G01N 21/43* | (2006.01) | |

(56) References Cited

U.S. PATENT DOCUMENTS

| | | | | |
|---|---|---|---|---|
| 5,923,027 | A * | 7/1999 | Stam et al. | 250/208.1 |
| 5,987,152 | A | 11/1999 | Weisser | |
| 6,137,529 | A * | 10/2000 | Kunimitsu et al. | 348/95 |
| 6,331,819 | B1 | 12/2001 | Hog | |
| 6,376,824 | B1 | 4/2002 | Michenfelder et al. | |
| 6,392,218 | B1 | 5/2002 | Kuehnle | |
| 6,452,148 | B1 | 9/2002 | Bendicks et al. | |
| 6,555,804 | B1 | 4/2003 | Blasing | |
| 6,614,015 | B1 | 9/2003 | Ba et al. | |
| 6,617,564 | B2 | 9/2003 | Ockerse et al. | |
| 6,841,767 | B2 | 1/2005 | Mindl et al. | |
| 6,968,073 | B1 * | 11/2005 | O'Boyle et al. | 382/104 |
| 7,208,962 | B2 | 4/2007 | Sun et al. | |
| 7,253,898 | B2 | 8/2007 | Saikalis et al. | |
| 7,259,367 | B2 | 8/2007 | Reime | |
| 7,609,857 | B2 | 10/2009 | Franz | |
| 7,612,356 | B2 | 11/2009 | Utida et al. | |
| 7,646,889 | B2 | 1/2010 | Tsukamoto | |
| 7,855,353 | B2 | 12/2010 | Blaesing et al. | |
| 7,863,568 | B2 | 1/2011 | Fleury | |
| 8,274,562 | B2 | 9/2012 | Walter et al. | |
| 8,541,732 | B2 | 9/2013 | Rothenhaeusler | |
| 8,913,132 | B2 | 12/2014 | Seger et al. | |
| 2002/0003571 | A1 * | 1/2002 | Schofield et al. | 348/148 |
| 2002/0081029 | A1 * | 6/2002 | Marugame | 382/190 |
| 2002/0148987 | A1 | 10/2002 | Hochstein | |
| 2003/0066955 | A1 | 4/2003 | Schaub et al. | |
| 2003/0201380 | A1 | 10/2003 | Ockerse et al. | |
| 2004/0004456 | A1 | 1/2004 | LeBa et al. | |
| 2004/0164981 | A1 | 8/2004 | Fujita et al. | |
| 2004/0165749 | A1 | 8/2004 | Holz et al. | |
| 2005/0035926 | A1 | 2/2005 | Takenaga et al. | |
| 2005/0063071 | A1 | 3/2005 | Wang et al. | |
| 2005/0178954 | A1 | 8/2005 | Yukawa | |
| 2005/0206511 | A1 | 9/2005 | Heenan et al. | |
| 2005/0231725 | A1 | 10/2005 | Franz | |
| 2005/0254688 | A1 | 11/2005 | Franz | |
| 2006/0076477 | A1 | 4/2006 | Ishikawa | |
| 2006/0163458 | A1 | 7/2006 | Reime | |
| 2006/0191215 | A1 | 8/2006 | Stark | |
| 2007/0075220 | A1 | 4/2007 | Kotani | |
| 2007/0216768 | A1 | 9/2007 | Smith et al. | |
| 2007/0267993 | A1 | 11/2007 | Leleve et al. | |
| 2007/0268470 | A1 | 11/2007 | Shibazaki | |
| 2008/0027607 | A1 | 1/2008 | Ertl et al. | |
| 2008/0049344 | A1 * | 2/2008 | DeWard et al. | 359/877 |
| 2008/0185603 | A1 | 8/2008 | Itoi et al. | |
| 2008/0265134 | A1 | 10/2008 | Kinoshita | |
| 2008/0296577 | A1 | 12/2008 | Yuan et al. | |
| 2009/0085755 | A1 | 4/2009 | Schafer et al. | |
| 2009/0128629 | A1 | 5/2009 | Egbert et al. | |
| 2009/0201366 | A1 | 8/2009 | Sase et al. | |
| 2010/0208060 | A1 | 8/2010 | Kobayashi et al. | |
| 2011/0031921 | A1 | 2/2011 | Han | |
| 2011/0043624 | A1 | 2/2011 | Haug | |
| 2011/0128543 | A1 | 6/2011 | Choi | |
| 2011/0204206 | A1 | 8/2011 | Taoka | |

| | | | |
|---|---|---|---|
| 2011/0253917 | A1 | 10/2011 | Rothenhaeusler |
| 2011/0273564 | A1 | 11/2011 | Seger et al. |
| 2012/0026318 | A1 | 2/2012 | Huelsen et al. |
| 2012/0026330 | A1 | 2/2012 | Huelsen et al. |
| 2012/0153154 | A1 | 6/2012 | Rothenhaeusler et al. |
| 2014/0321709 | A1 | 10/2014 | Kasahara et al. |
| 2015/0034827 | A1 | 2/2015 | Kroekel |
| 2015/0070499 | A1 | 3/2015 | Roelke et al. |

FOREIGN PATENT DOCUMENTS

| | | | | |
|---|---|---|---|---|
| DE | 44 17 385 | | 11/1995 | |
| DE | 195 04 606 | | 8/1996 | |
| DE | 197 04 818 | | 8/1997 | |
| DE | 202 07 170 | | 8/2002 | |
| DE | 102 30 200 | | 1/2004 | |
| DE | 197 00 665 | | 7/2004 | |
| DE | 103 03 046 | | 10/2004 | |
| DE | 103 16 794 | | 11/2004 | |
| DE | 103 22 010 | | 12/2004 | |
| DE | 103 55 205 | | 7/2005 | |
| DE | EP 1580092 | * | 9/2005 | B60R 1/08 |
| DE | 102004015040 | | 10/2005 | |
| DE | 102004037871 | | 3/2006 | |
| DE | 102005004513 | | 3/2006 | |
| DE | 102006008274 | | 8/2007 | |
| DE | 102006010671 | | 9/2007 | |
| DE | 102006022404 | | 11/2007 | |
| DE | 102007061725 | | 6/2009 | |
| DE | 102008043737 | | 5/2010 | |
| DE | 102008062977 | | 6/2010 | |
| DE | 102009000003 | | 7/2010 | |
| DE | 102009000004 | | 7/2010 | |
| DE | 102009000005 | * | 7/2010 | B60R 1/00 |
| EP | 0 832 798 | | 4/1998 | |
| EP | 1 580 092 | | 9/2005 | |
| EP | 1 764 835 | | 3/2007 | |
| EP | 1 923 695 | | 5/2008 | |
| JP | S57-004133 A | | 1/1982 | |
| JP | S60-125260 U | | 8/1985 | |
| JP | H04-061379 A | | 2/1992 | |
| JP | H11-234474 A | | 8/1999 | |
| JP | 2003-315256 A | | 11/2003 | |
| JP | 2005-292544 | | 10/2005 | |
| JP | 2006-184844 | | 7/2006 | |
| JP | 2007-309655 A | | 11/2007 | |
| JP | 2009-092453 A | | 4/2009 | |
| JP | 2009-098477 A | | 5/2009 | |
| JP | 2010-096604 A | | 4/2010 | |
| JP | 2010096604 | * | 4/2010 | B60S 1/08 |
| WO | WO 03/029757 | | 4/2003 | |
| WO | WO 2005/075248 | | 8/2005 | |
| WO | WO 2006/015905 | | 2/2006 | |
| WO | WO 2006/024247 | | 3/2006 | |
| WO | WO 2006/121954 | | 11/2006 | |
| WO | WO 2009/020918 | | 2/2009 | |
| WO | WO 2010/072198 | | 7/2010 | |
| WO | WO 2010/076064 | | 7/2010 | |
| WO | WO 2012/163341 | | 12/2012 | |

OTHER PUBLICATIONS

International Search Report of the International Searching Authority for International Application PCT/DE2011/001749, mailed Mar. 29, 2012, 4 pages, European Patent Office, HV Rijswijk, Netherlands.

PCT International Preliminary Report on Patentability including English Translation of PCT Written Opinion of the International Searching Authority for International Application PCT/DE2011/001749, issued Jun. 4, 2013, 6 pages, International Bureau of WIPO, Geneva, Switzerland.

Chinese Office Action in Chinese Patent Application No. 201180056008.4, mailed Dec. 14, 2015, 10 pages, with English translation, 12 pages.

\* cited by examiner

DETECTION OF RAINDROPS ON A PANE BY MEANS OF A CAMERA AND LIGHTING

FIELD OF THE INVENTION

The invention relates to a device and a method for detecting raindrops on a pane by means of a lighting source and a camera.

BACKGROUND OF THE INVENTION

In WO2010/072198 A1 rain detection is described with the aid of a camera, which is used for automotive driver assistance functions. For rain detection bifocal optics are used, which form a sharp image of a portion of the windscreen onto a portion of the image chip or image sensor of the camera.

A disadvantage of this idea is the fact that an additional optical element is introduced, whose edge causes serious disturbances both in the beam path for the rain sensor area of the image chip as well as in the region for the driver assistance functions in the vicinity of the edge. In particular for implementations with small dimensions, the focus conditions for the driver assistance and the rain sensor area are strongly different, what must be compensated by an increased thickness of the optical element, thus leading to increased disturbances and a broad, non-usable region on the image chip around the edge.

Another disadvantage results from different pane inclinations, which have different optical distances between rain sensor detection area on the image chip and corresponding rain sensor surface on the pane. To continue to ensure a sharp optical imaging, for each modified installation situation the thickness of the optical element must be adapted.

In order to detect raindrops also at night, it is proposed in WO 2010/072198 A1 to couple light via a coupling element into the windscreen and to guide it via total reflection in the pane. By a decoupling element the totally reflected light is decoupled in the direction of the camera. When there are water drops on the windscreen, a part of the light is decoupled and is no longer totally reflected to the decoupling element. It is also disadvantageous here that for each modified pane inclination the integrated camera lighting unit must be mechanically adapted to the modified installation condition.

In U.S. Pat. No. 7,259,367 B2 also by means of a camera rain sensing is proposed, which provides a large-area lighting of the passing-through window of the camera opening angle with the pane. The camera focus is set to almost infinite and thus can be simultaneously used for driver assistance applications. Because of the imaging on the far range raindrops are noticeable only as disturbances in the image, which are detected by complex differential measurements of the images recorded with light pulsed or modulated in synchronization with the pixel clock.

However, computer simulations and measurements show that with this type of lighting only a very small portion of the light is reflected at the raindrops back into the camera. This fact leads to a poor signal to noise ratio and consequently to an insecure rain detection.

SUMMARY OF THE INVENTION

It is, therefore, an object of an embodiment of the present invention to overcome the mentioned disadvantages of the devices or methods known from prior art.

This object can be achieved by a device for detecting rain, according to an embodiment of the invention, which comprises a camera and a lighting source. The camera is disposed behind a pane, in particular in the interior of a vehicle e.g. behind a windscreen, and is focused onto a far range that lies in front of the pane. The camera preferably comprises an objective for focusing and an image sensor, e.g. a CCD or CMOS sensor. The lighting source for generating at least one light beam directed towards the pane directs the at least one light beam towards the pane, such that at least one beam that is reflected from the outer face of the pane (or partial beam of the light beam directed towards the pane) impinges on the camera. The lighting source can be embodied as one or more light emitting diodes (LEDs) or as a light band.

The light quantity of the beam impinging on the at least one camera can be measured by the camera.

The invention provides a simple but reliable possibility to detect rain with a vehicle camera, in particular with a driver assistance camera. Since essentially only one light quantity is to be measured, no complex image processing algorithm is needed. By the active lighting the device is relatively less interference-prone to external influences such as sun reflexes and hard shadows.

The rain quantity, for example with multi-beam lighting sources, can be determined via a reduction of the light quantity of all light reflexes (on the image sensor) of the outer windscreen and/or via the number of the influenced light reflexes.

In a preferred form of embodiment the angle of incidence of the light beam generated by the lighting source is set such that the beam (part), which impinges on the outer face of the pane, is more reflected than decoupled from the pane, when there is no rain on the outer face of the pane.

According to an advantageous form of embodiment, the device comprises an evaluation unit, which determines from the measured light quantity of the beam that is reflected at the outer face of the pane whether and if so how much rain is present on the outer face of the pane.

Preferably, for determining rain the evaluation unit can compare the measured light quantity of the beam that is reflected at the outer face of the pane with a threshold value. The threshold value may be adapted in particular to a modified intensity of the lighting and/or to a modified sensitivity of the camera, e.g. by regular calibrations with a dry pane. Also, several threshold values can be used.

Advantageously, the evaluation unit determines a time variation of the light values measured by the image sensor of the camera of the beam that is reflected at the outer face of the pane. For this purpose, a series of images can be recorded with the camera.

In a preferred form of embodiment, the lighting source directs the at least one light beam towards the pane, such that the beams reflected from the inner and outer face of the pane impinge as at least two spatially separated beams on the camera. The light quantities of the at least two beams impinging on the camera can be measured in this case by the camera. The beam, reflected (directly) on the inner face of the pane, which impinges on the camera, in this case preferably serves as a reference signal, since the light quantity of this beam remains constant in case of presence or absence of raindrops on the outer face of the pane.

This type of detection with the lighting proposed here is not necessarily dependent on a camera, but can be utilized by means of each optical sensor, which can determine the light quantities of two spatially separated beams. The advantage of the introduced method of detection compared to conventional diode-rain sensors is based on the fact that no coupling optics is needed and simultaneously, a reference beam is available for a comparative measurement.

Preferably, the camera is used for one or more further driver assistance functions, which are based on an evaluation of the far range imaged in focused manner.

According to an advantageous embodiment of the invention, the lighting source is structurally integrated into the camera or into the housing of the camera. Here, the lighting source can be preferably disposed within the camera housing below a view shield or a view funnel of the camera.

Advantageously, here the lighting source generates light in the infrared wavelength range, and the view shield is permeable in the infrared wavelength range at least in a portion, which is located above the lighting source or in the beam direction of the lighting source.

In this case, the lighting source can be arranged in particular on a circuit carrier or a circuit board of the camera.

Preferably, the lighting source generates only light having a wavelength in a certain wavelength range, such as e.g. in the (near) infrared wavelength range.

In the beam path of the camera, a first spectral filter is arranged in that region, in which the at least two spatially separated reflected beams are passing through. The first spectral filter is at least to a large extent permeable to light having a wavelength in this specific wavelength range (e.g. infrared-permeable).

Advantageously, a second spectral filter is arranged in that region of the beam path, in which the at least two spatially separated reflected beams do not pass through, wherein the second spectral filter blocks light having a wavelength in the specific wavelength range (e.g. IR-cut filter).

The first or both spectral filters can preferably be applied directly on pixels of the image sensor of the camera.

In an advantageous form of embodiment, the lighting source generates a focused light beam.

Preferably, the light beam generated by the lighting source can be directed onto the pane by means of a light guide such as e.g. an optical fiber.

The invention further relates to a method for detecting rain on the outer face of a pane. Also for this, the prerequisites are a camera disposed behind the pane, which is focussed on a far range in front of the pane, and a lighting source for generating at least one light beam directed towards the pane. The lighting source directs the at least one light beam towards the pane such that at least one beam that is reflected from the outer face of the pane impinges on the camera. The light quantity of the at least one beam that is reflected from the outer face of the pane is measured by means of the camera. By evaluating the measured light quantity of the at least one beam that is reflected from the outer face of the pane, the presence or absence of rain on the outer face of the pane can be determined.

A preferred method for detecting rain on the outer face of a pane makes use of a device according to an embodiment of the invention. With the camera at first, a first image is recorded with the lighting source turned off. Then a second image is recorded with the lighting source turned on. The difference image from the second image and the first image is formed. In the difference image, the light quantity of the at least one beam that is reflected at the outer face of the pane is evaluated for detecting rain on the outer face of the pane.

In an advantageous use of visible light as lighting it must be ensured that road users are not disturbed by the lighting.

For this purpose, it is proposed to use a short visible light pulse, adapted by the intensity of the external brightness. This would require only a short exposure time and image recording time for the rain sensor image, what in turn has little influence on the driver assistance function. Such a light pulse would be seen during daylight only when looking directly at the lighting. At night only little light is required for rain detection. Here, the intensity can be down-regulated appropriately, so that also at night the lighting does not have a disturbing effect.

A preferred adaptation of the lighting intensity—regardless of the used wavelength range—provides a further advantage. The rain sensor light reflexes are also clearly visible during the day and at night it is avoided that the images are in saturation and would thus prevent a quantitative evaluation.

The lighting can be advantageously realized via individual LEDs, which e.g. are arranged in series. Alternatively, a light band could be used. Preferably, here a sufficiently directed radiation characteristics of e.g. less than ±20° is guaranteed.

BRIEF DESCRIPTION OF THE DRAWINGS

In the following, the invention will be explained on the basis of figures and exemplary embodiments.

DETAILED DESCRIPTION OF THE PREFERRED EMBODIMENTS

Figure 1:
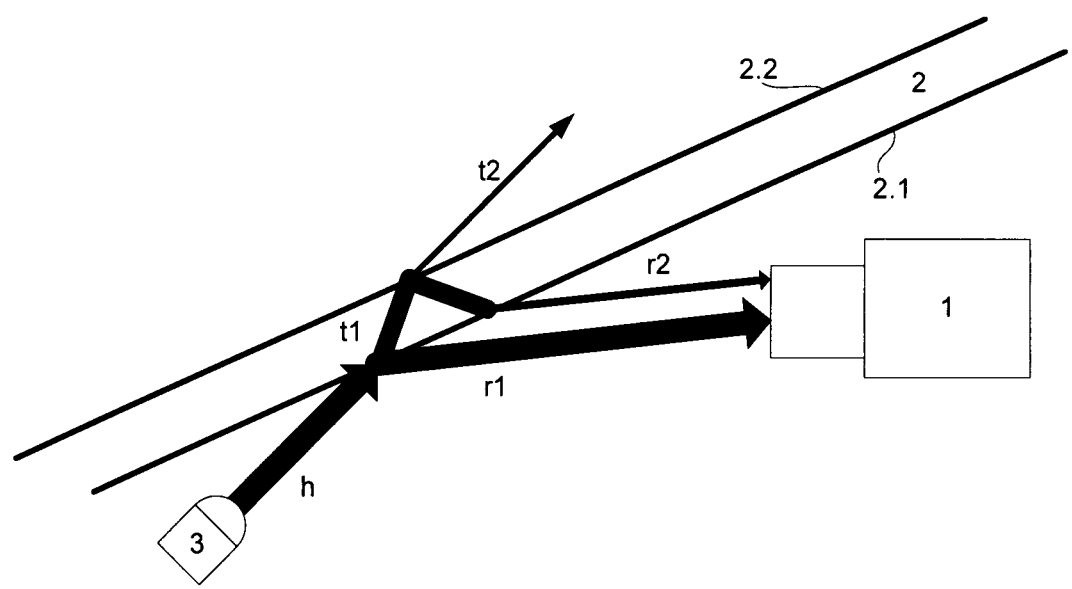
FIG. 1 schematically shows the basic principle of a possible arrangement of lighting source and camera with beam paths with a dry pane.

FIG. 1 illustrates the functional principle of a first form of embodiment of the invention. The presented rain detection is based on a camera (1) focused onto the far range and a lighting (3), which in contrast to the large-scale lighting from U.S. Pat. No. 7,259,367 B2 uses one or more focused beams (h).

A light beam (h) generated by a lighting source (3) is directed towards the pane (2) such that the beams reflected from the inner (2.1) and outer face (2.2) of the pane impinge as two spatially separated beams (rl, r2) on the objective or the camera (1). Due to the focussing on the far range, the boundary of the beam bundle is imaged only blurred on the image chip (5). But both beams (r1, r2) are sufficiently separated and their respective light quantity can be measured with the image sensor (5).

In this form of embodiment, the main beam (h) of the lighting source (3) is used, therefore, the light of the lighting source can be preferably focused. The portion (r1) reflected at the air-pane-interface (or pane inner face (2.1)) of the main beam serves as a reference beam. From the portion which is transmitted into the pane (t1), that portion is used as a measurement beam (r2), which is reflected at the pane-air-interface (or pane outer face (2.2)) and impinges on the camera (1). Not shown is that portion of the beam, which is repeatedly reflected inside the pane (2) (on the inner face (2.1) pane-air, after it was reflected at the outer face (2.2) pane-air).

This arrangement offers the advantage of a distinct signal change with rain (4) on the pane outer face (2.2), as is explained with reference to FIG. 2.

Figure 2:
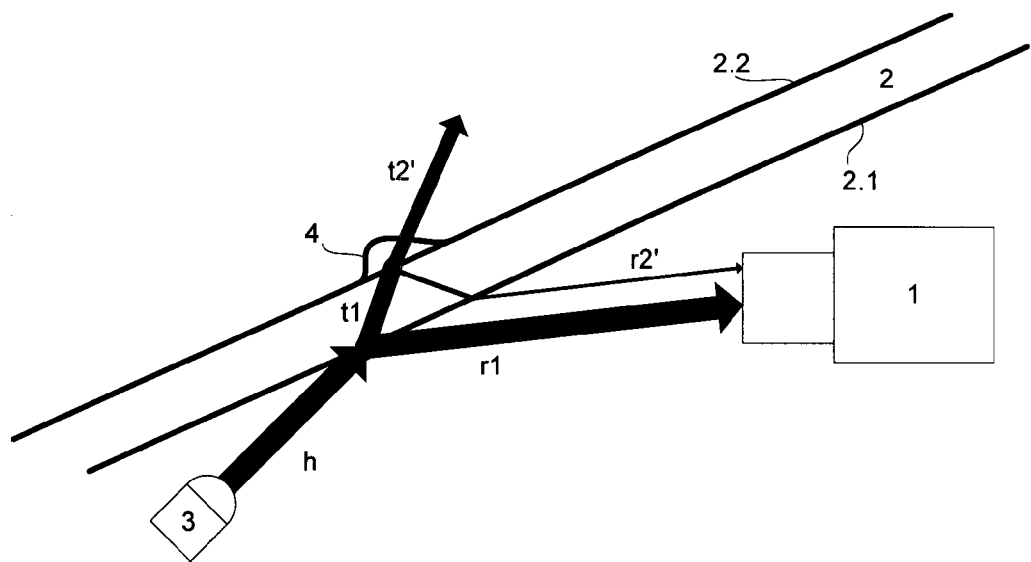
FIG. 2 schematically shows the modified beam paths with rain on the pane.

When the outer face (2.2) of the windscreen (2) is wetted with rain (4) the majority of light (tl) is decoupled as a decoupled transmitted beam (t2'), so that the reflected portion (r2') is weakened accordingly (see FIG. 2). The beam (rl) reflected from the inner face (2.1) is unaffected.

By comparing the measured light quantities of both beams (r1 to r2 or r2'), thus the signal (r2') reduced in case of rain (4) can be easily measured and a windscreen wiper can be activated accordingly.

In order not to irritate the driver and other road users by the lighting (3), in particular near infrared light can be used, for which usually the used CCD or CMOS imaging chips (5) have a high sensitivity.

To become insensitive to disturbances such as noise, daylight and sunlight and other sources of artificial light, it is proposed to partially or completely timely modulate the lighting source (3) preferably synchronously with the image readout clock, so that disturbances can be deducted via simple differential methods. This is one way to improve the signal to noise ratio. A further possibility consists in an appropriate spectral filtering: the section of the image chip (5), on which the beam pairs (r1, r2/r2') impinge, can be provided with a spectral band pass, which has a high permeability for the wavelength of lighting (3).

Figure 3:
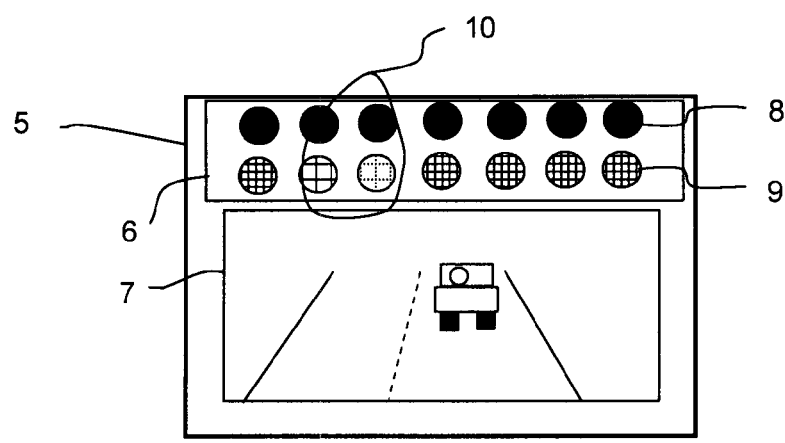
FIG. 3 shows signals detected by an image sensor of a camera, which suggest rain.

FIG. 3 shows in the upper part (6) of the image sensor (5), which serves for rain detection, seven pairs of lighting reflexes (8, 9) each, which e.g. are generated by seven LEDs as lighting source (3). These are not sharply imaged but are perceptible, due to the camera (1) focused onto infinity. In particular, the light intensity or quantity can be measured. The upper lighting reflexes (8) are generated by beams (r1) reflected at the inner face (2.1) of the windscreen (2), the lower lighting reflexes (9) are generated by beams (r2, r2') reflected at the outer face of the windscreen.

In order to realize driver assistance functions simultaneously with the camera image, the light beam pairs (8, 9) may not interfere with the driver assistance image (7). For this purpose, a portion is selected (6) in FIG. 3, which lies outside of the driver assistance image (7) on the image chip (5).

FIG. 3 thus shows an exemplary proportioning of the driver assistance portion (7) and the rain sensor area (6) on the image chip (5). The lighting reflexes from the outer windscreen (9), above which lies a raindrop (4), are weakened in intensity. These lighting reflexes (9) originate from beams (r2') reflected at the outer face (2.2) of the windscreen (2) and are of reduced intensity, since a large part of the beam (t1) transmitted into the windscreen (2) is decoupled (t2') from the windscreen by raindrops (4) and thus is not reflected (r2') back to the camera (1). Consequently, these lighting reflexes (9) carry the information, whether there is rain (4) on the outer face (2.2) of the pane (2), and their light quantity could be used alone as a measurement signal. The evaluation can be made e.g. by comparison with a threshold value, by comparing the light quantities of several of these lighting reflexes (9) with each other and/or by analysis of the temporal variations of the light quantity of at least one of these lighting reflexes (9).

In order to avoid disturbances by the lighting (3) as far as possible, in addition an infrared cut filter can be vapor-deposited on a cover glass of the image chip (5) up to the upper edge of the driver assistance area (7). In addition, as already mentioned above, a band-pass filter for the wavelength of lighting (3) can be vapor-deposited above the rain sensor detection area (6).

Alternatively, the filter may also be applied directly to the pixels of the image sensor (5). This would have the advantage that a parallax offset is avoided, which is generated by the edge of the different filters for the rain sensor area (6) and the driver assistance area (7) on the cover glass. A process would be advantageous here, which corresponds to the current application of the pixel color filter. Thereby, the two areas (6, 7) can be separated pixel accurately, avoiding additional mechanical tolerance allowances, which result from the production process. In this context one would omit the application of color filters (R, G, B) for the rain sensor area (6) and thereby increase the sensitivity for the detection of rain.

Figure 4:
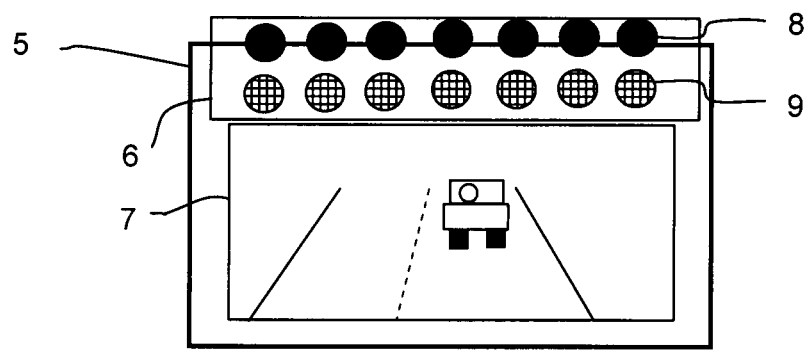
FIG. 4 shows an arrangement, in which the beams reflected at the inner face of the pane are imaged only partially on the image sensor of the camera.

FIG. 4 shows a partial illustration of the lighting spots or reflexes (8) on the image chip (5).

According to a variant of embodiment, the upper area for the rain sensor (6) must not necessarily contain the reflexes (8) from the inner surface of the windscreen (2.1), since the modification of the light due to rain (4) is visible on the lower light spots (9). These alone can suffice as a measurement signal and can be compared e.g. with a light quantity threshold value. If the measurement signal is greater than or equal to the threshold value, it is detected that the pane is dry. If, however, the measurement signal is below the threshold value, rain (4) is detected on the outer face (2.2) of the pane (2). The more the measurement signal falls below the threshold value, the more rain is on the pane (2). This variant of embodiment offers the possibility that the area for the rain sensor (6) can be considerably reduced.

However, by means of this the upper spot (8) from FIG. 4 is not applicable in this variant of embodiment as the reference light quantity, what could have an adverse effect in case of lighting fluctuations. To avoid this disadvantage, the upper rain sensor area (6) can preferably be reduced only until the upper light spots (8) remain partly visible. This is illustrated in FIG. 4.

Figure 5:
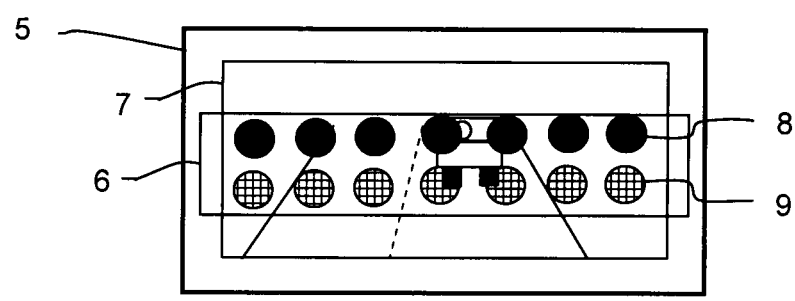
FIG. 5 shows an arrangement, in which the reflected beams are imaged superimposed to the focused far range on the image sensor.

FIG. 5 shows a spatial overlapping of the driver assistance area (7) or of the far range imaging with the rain sensor area (6) or the blurred imaging of the lighting reflexes (8, 9). In case the image chip (5) or the structural integration of the lighting should not allow for a sufficient size for the spatially separated illustration of the light spots (8, 9) and of the driver assistance area (7), then e.g. alternately with the driver assistance image an extra image of the rain sensor light spots could be recorded. For this purpose, the lighting (3) is turned off during the recording of the driver assistance image and is turned on again for recording of the rain sensor image.

This offers for the rain sensing simultaneously the advantage that a difference image with the previous driver assistance image can be formed, thus strongly reducing the background signal and ideally leaving only the rain sensor image of the light spots (8, 9).

Often, driver assistance cameras (1) have an infrared cut filter to reduce the spectral requirements to optics and/or to permit a better color recognition. The color filters (R, G, B) on the individual pixels of the image chips (5) used today in the infrared spectral range often again have a high transmission and thus deteriorate the color selectivity.

With a spatial overlapping of the driver assistance area (7) with the rain sensor area (6) as is shown in FIG. 5 either no infrared cut filter can be used or the wavelength of the lighting (3) should be pushed into the visible area.

If better color filters (R, G, B) are used, which are no longer permeable to the infrared light, by a skilled selection of the color filter sample the rain sensor spots (8, 9) and the driver assistance image (7) can be recorded simultaneously and spatially overlapped.

Figure 6:
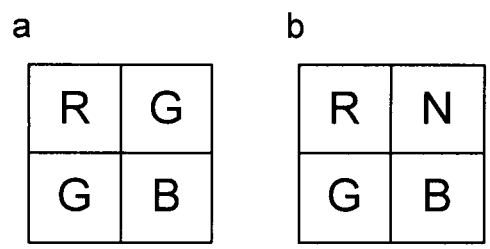
FIG. 6a shows a Bayer pattern as a filter pixel matrix.
FIG. 6b shows a modified Bayer pattern with a colorless filter pixel element.

FIG. 6a shows the very common Bayer pattern R-G-G-B, red-green-green-blue.

FIG. 6b shows an example for a modified pattern R-N-G-B, in which the neutral pixel (N) has absolutely no color filter and thus is permeable for the visible and the infrared light. Only these "white" pixels (N) are used for rain sensing. In addition, with a separation in time of the two recordings they could also be used for driver assistance functions to increase the dynamics of the image chips (5) and the sensitivity in dark situations.

In FIGS. 1 and 2 a lighting source (3) is shown with a beam path, which still causes merely a partial reflection but lies close to the angle of the total reflection in the pane (2). In the arrangement shown there, the signal change in the presence of raindrops (4) on the pane (2) is particularly distinctive.

However, the lighting source (3) is arranged far below the camera (1) outside the compact camera housing, entailing structural limitations and disadvantages.

Figure 7:
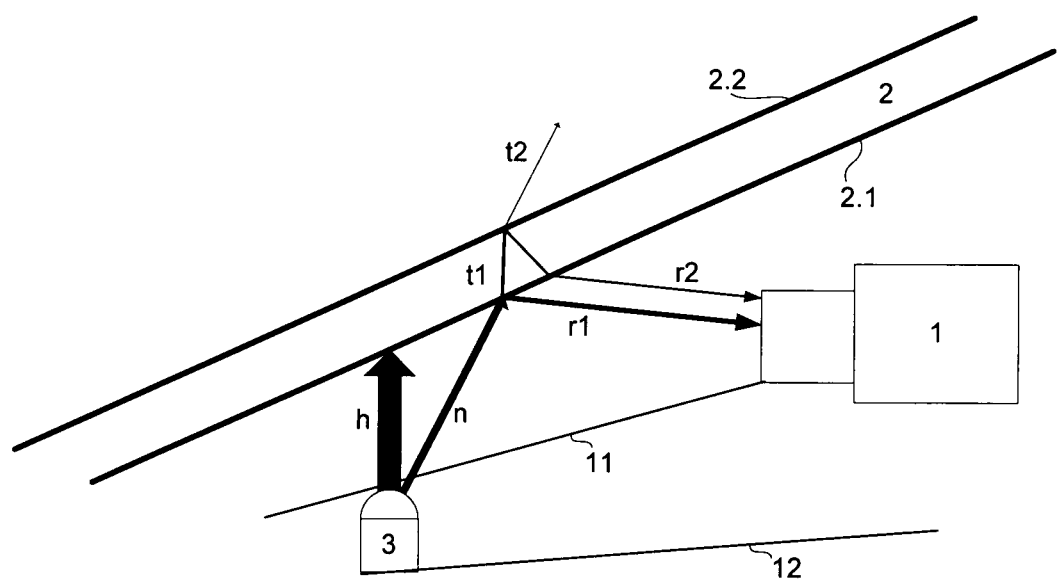
FIG. 7 schematically shows an alternative arrangement of lighting source and camera, in which the lighting source is arranged on a circuit carrier below the view shield of the camera.
Figure 8:
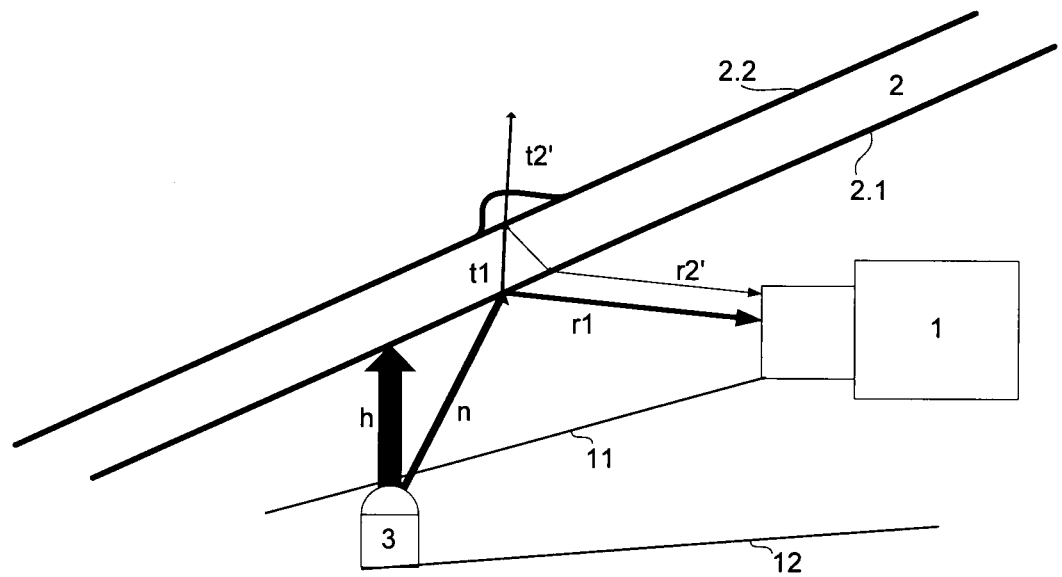
FIG. 8 schematically shows the modified beam paths of the alternate arrangement with rain on the pane.

FIGS. 7 and 8 show an alternative arrangement, which offers the advantage that the lighting source (3) can be integrated into the camera (1), in more detail into the camera housing.

When the opening angle of the lighting (usually by means of LEDs) is large enough, the lighting source (3) can also be placed within the camera (1), e.g. as is shown on a circuit board (12) of the camera system. This results in a significant integration advantage.

The relative effect between the beam (r2) reflected at the outer face (2.2) and the beam (r1) reflected at the inner face of the secondary beam (n) of the lighting source (3) turns out to be easily measurable and sufficient to reliably recognize raindrops (4) on the pane (2).

If infrared light is used for the lighting and the lighting source (3) is arranged as shown in FIG. 7 below a view shield or a view funnel (11), the view shield (11) must be be transparent to infrared light at least in the region through which the light beam (n) enters from the lighting source (3) to the pane (2).

FIG. 8 shows the change in the presence of raindrops (4) on the outer face (2.2) of the pane (2):

Also here raindrops (4) effect a stronger decoupling (t2') of light from the pane in the area in front of the pane. Thus, from the camera (1) a reduced intensity of the partial beam (r2') is measured, which was reflected at the outer face (2.2) of the pane (2).

In this form of embodiment, not the main beam (h) of the lighting source is used, but a secondary beam (n), which impinges on the camera (1) via reflections at the pane (2) as at least two spatially separated partial beams (r1; r2; r2'). Otherwise the beam paths and portions are comparable to those shown in FIGS. 1 and 2, the reference numerals are used accordingly identically.

The mode of detection shown in FIGS. 1 and 2 as well as in FIGS. 7 and 8, similar to the classical optical rain sensor, is based on detecting a reduction in light, if the outer face (2.2) of the pane (2) is wet.

In addition, with this arrangement also the light (rh) of the main beam (h) reflected at the raindrop (4) can be used to detect rain. This is shown in FIGS. 9 and 10.

Figure 9:
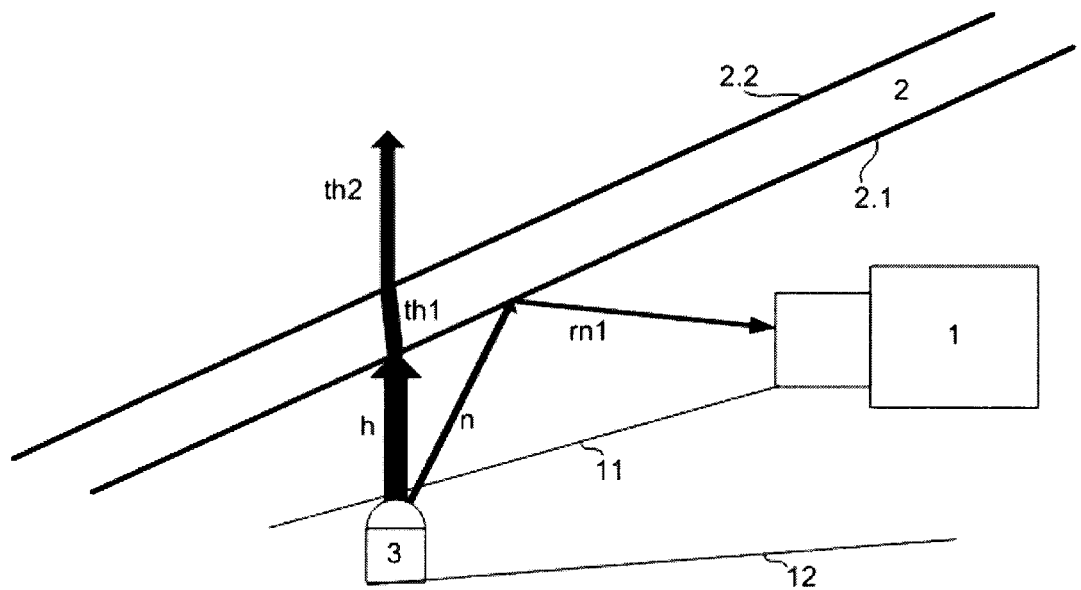
FIGS. 9 and 10 schematically show an additional possibility to detect rain with the alternative arrangement by measuring a portion of the main beam of the lighting source that is reflected in the raindrop, which impinges on the camera when there is rain on the pane.

FIG. 9 shows the situation with a dry pane (2): while as in FIG. 7 the portion (rnl) reflected by the secondary beam (n) at the inner face (2.1) of the pane (2) causes a reference intensity on the image sensor (5), the main beam (h) is not shown on the image sensor. As long as exclusively lighting reflexes of the reference beam (rnl) are detected, it can therefore be recognized that there is no rain (4) on the pane (2).

Figure 10:
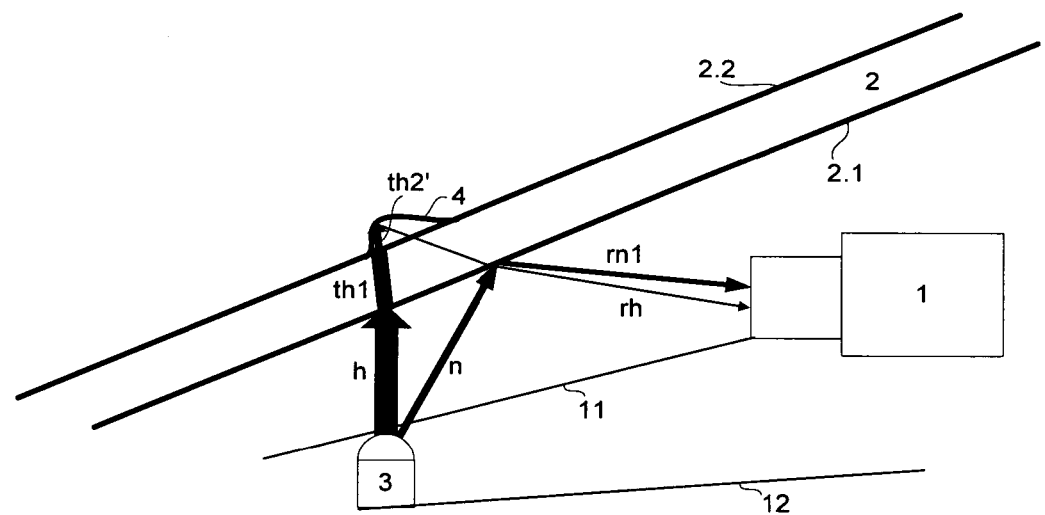

As is shown in FIG. 10, raindrops (4) effect on the outer face (2.2) of the windscreen (2) that a small portion (rh) of the main beam is reflected in the raindrop (4) such that it impinges on the camera (1). Consequently, the occurrence of one or more lighting reflexes in addition to lighting reflexes of the reference beam (rnl) suggests the presence of rain (4).

Of course, also both modes of detection (from FIGS. 7+8 and from FIGS. 9+10) can be combined in order to improve the rain detection and to make more robust against interfering environmental influences (changing background, sun reflexes, headlights etc.).

Figure 11:
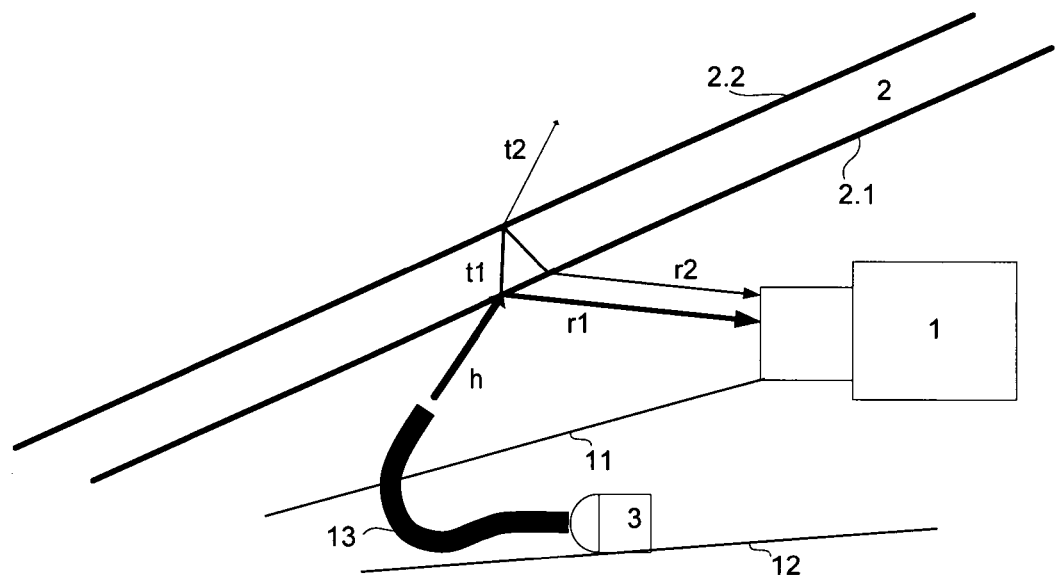
FIG. 11 shows an arrangement, in which the light from the lighting source is guided via a light guide onto the pane.

FIG. 11 shows a further example of embodiment, in which the arrangement includes a light guide (13). To simplify the integration of the lighting (3) into the housing of the camera (1) and for guiding the light beam (h) to a certain position of the windscreen (2), here a light guide (13) is used. Hereby, in particular the positioning of the light reflex (9) (for the rain detection) of the partial beam (r2; r2'), which is reflected at the outer face (2.2) of the windscreen (2), on the image chip (5) in a region, which lies outside of the driver assistance area (7), can be facilitated. The principle of rain detection is the same as has been explained in FIGS. 7 and 8, except that instead of the secondary beam (n in FIGS. 7+8) of the lighting (3) the main beam (h) is guided accordingly by means of the light guide (13).

REFERENCE NUMERALS

1 Camera
2 Pane
2.1 Inner face of the pane
2.2 Outer face of the pane
3 Lighting source
4 Rain, raindrops
5 Image Sensor
6 Rain sensor area
7 Driver assistance area
8 Lighting reflex from pane inner face
9 Lighting reflex from pane outer face
10 Signal change with raindrops
11 View shield
12 Circuit carrier
13 Light guide
h Main beam
n Secondary beam
r1 Portion of h or n, which is reflected at the pane inner face
t1 Portion of h or n, which is transmitted at the pane inner face
r2 Portion of t1, which is reflected at the pane outer face
t2 Portion of t1, which is transmitted at the pane outer face
r2' Corresponds to r2 with rain on the pane outer face
t2' Corresponds to t2 with rain on the pane outer face
th1 Portion of the main beam, which is transmitted at the pane inner face
th2 Portion of th1, which is transmitted at the pane outer face
th2' Corresponds to th2 with rain on the pane outer face
rh Portion of th2', which is reflected in the raindrop to the camera rn1 Portion of n, which is reflected at the pane inner face
R Filter element, which is permeable to light in the red wavelength range
G Filter element, which is permeable to light in the green wavelength range
B Filter element, which is permeable to light in the blue wavelength range
N Filter element, which is permeable to light in the visible and/or infrared wavelength range

The invention claimed is:

1. A device for detecting rain (4) on an outer surface of a pane, comprising
  a camera disposed behind an inner surface of the pane (2), wherein the camera (1) is focused onto a far range that lies in front of the outer surface of the pane (2), and
  a lighting source (3) adapted to generate a source light beam and configured and arranged to direct the source light beam (h; n) through air onto the inner surface of the pane (2) so as to cause a resultant transmitted beam that is transmitted in the pane and impinges on the outer surface within the pane and is partially reflected from the outer surface (2.2) within the pane (2) to cause a partially reflected beam (r2; r2') that impinges on the camera (1); and
  wherein the camera is configured and adapted to measure a light quantity of the partially reflected beam (r2; r2') impinging on the camera.

2. The device according to claim 1, wherein an angle of incidence of the source light beam (h; n) onto the inner surface of the pane is set up such that the resultant transmitted beam (tl), which is transmitted in the pane and impinges on the outer surface (2.2) of the pane (2), is more reflected to form said partially reflected beam than decoupled (t2) out of the pane, when there is no rain (4) on the outer surface (2.2) of the pane (2).

3. The device according to claim 1, further comprising an evaluation unit configured to determine from the measured light quantity of the partially reflected beam whether or not there is rain (4) on the outer surface (2.2) of the pane (2).

4. The device according to claim 3, wherein the evaluation unit is configured to compare the measured light quantity of the partially reflected beam (r2; r2') with a threshold value.

5. The device according to claim 3, wherein the evaluation unit is configured to determine a time variation of the measured light quantity.

6. The device according to claim 1, wherein the lighting source (3) is configured and arranged to direct the source light beam (h; n) towards the pane (2) such that the partially reflected beam (r2 or r2') that is partially reflected from the outer surface of the pane and another beam (rl) that is reflected from the inner surface (2.1) of the pane respectively impinge as two spatially separated beams (rl; r2 or r2') on the camera (1), and respective light quantities of the two spatially separated beams (rl; r2 or r2') impinging on the camera (1) can be respectively measured by the camera (1).

7. The device according to claim 1, wherein the lighting source (3) is structurally integrated into a housing of the camera (1).

8. The device according to claim 7, wherein the lighting source (3) is arranged below a view shield (11) of the camera (1).

9. The device according to claim 8, wherein the lighting source (3) is configured to generate light of the source light beam in an infrared wavelength range and the view shield (11) is permeable in the infrared wavelength range at least in a portion of the view shield, which is located above the lighting source (3).

10. The device according to claim 7, wherein the lighting source (3) is arranged on a circuit carrier (12) of the camera (1).

11. The device according to claim 1, wherein the lighting source (3) is configured to generate the source light beam with only light having a wavelength in a specific wavelength range, and wherein a first spectral filter is arranged in the beam path of the camera (1) in a region, through which the partially reflected beam (r2; r2') passes, and wherein the first spectral filter is permeable to light having a wavelength in the specific wavelength range.

12. The device according to claim 11, wherein the lighting source (3) is configured and arranged to direct the source light beam (h; n) towards the pane (2) such that the partially reflected beam (r2 or r2') and another beam (rl) that is reflected from the inner surface (2.1) of the pane respectively impinge as two spatially separated beams (rl; r2 or r2') on the camera (1), and respective light quantities of the two spatially separated beams (rl; r2 or r2') impinging on the camera (1) can be respectively measured by the camera (1), wherein a second spectral filter is arranged in a region of the beam path, through which the two spatially separated beams (rl; r2 or r2') do not pass, and wherein the second spectral filter blocks light having a wavelength in the specific wavelength range.

13. The device according to claim 12, wherein the camera (1) comprises an image sensor (5), and wherein the first spectral filter or the first and second spectral filters are applied directly on pixels of the image sensor (5).

14. The device according to claim 1, wherein the lighting source (3) is configured to generate a focused light beam (h) as the source light beam.

15. The device according to claim 1, further comprising a light guide, wherein the source light beam (h) generated by the lighting source (3) is directed by the light guide (13) and emitted from the light guide through the air onto the inner surface of the pane (2).

16. A method for detecting rain (4) on the outer surface (2.2) of the pane (2) by the device according to claim 1, comprising the steps:
  with the camera, recording a first image with the lighting source (3) turned off,
  with the camera, recording a second image with the lighting source (3) turned on,
  forming a difference image from the second and first images, and
  in the difference image, evaluating a light quantity of the partially reflected beam (r2; r2;') to detect whether there is rain (4) on the outer surface (2.2) of the pane.

17. The device according to claim 1, wherein the pane and the lighting source are configured and arranged so that the source light beam is directed through the air directly onto the inner surface of the pane, and wherein the inner surface of the pane forms an air-pane-interface for the source light beam.

18. The device according to claim 1, not including an optical coupling element on the inner surface of the pane for coupling the source light beam into the pane.

19. The device according to claim 1, wherein the light source is configured and arranged to direct the source light beam onto the inner surface of the pane at an incidence angle such that the resultant transmitted beam is always only partially reflected from the outer surface within the pane including when there is rain on the outer surface and when there is no rain on the outer surface.

20. A method for detecting rain (4) on an outer surface (2.2) of a pane (2), comprising the steps:

providing a camera (1) disposed behind an inner surface of the pane (2) and focused onto a far range in front of the outer surface of the pane, with a lighting source (3), generating a source light beam (h; n), and directing the source light beam (h; n) through air onto the inner surface of the pane (2) so as to cause a resultant transmitted beam that is transmitted in the pane and impinges on the outer surface within the pane and is partially reflected from the outer surface (2.2) within the pane (2) to cause a partially reflected beam that impinges on the camera (1), using the camera, measuring a light quantity of the partially reflected beam (r2; r2'), and evaluating the measured light quantity of the partially reflected beam (r2; r2') to detect whether there is rain (4) on the outer surface (2.2) of the pane (2).

21. A device for detecting rain on an outer surface of a pane, comprising:

a light source arranged behind an inner surface of said pane, adapted to generate a source light beam, and configured and arranged to direct said source light beam through air onto said inner surface of said pane at an incidence angle so as to cause a resultant first transmitted beam that is transmitted within said pane and impinges on said outer surface within said pane, and such that said first transmitted beam is only partially reflected from said outer surface internally in said pane to cause a second reflected beam that is emitted through said inner surface out of said pane; and a camera that is arranged behind said inner surface of said pane, and is focused onto a far range that lies in front of said outer surface of said pane, and is configured and arranged to receive said second reflected beam and measure a light quantity of said second reflected beam.

22. The device according to claim 21, wherein said pane and said light source are configured and arranged so that said source light beam is directed through said air directly onto said inner surface of said pane, and wherein said inner surface of said pane forms an air-pane-interface for said source light beam.

23. The device according to claim 21, not including an optical coupling element on said inner surface of said pane for coupling said source light beam into said pane.

24. The device according to claim 21, wherein said light source is configured and arranged to direct said source light beam onto said inner surface of said pane at such a value of said incidence angle such that said first transmitted beam is always only partially reflected from said outer surface internally in said pane including when there is rain on said outer surface and when there is no rain on said outer surface.

* * * * *